(12) United States Patent
Takizawa et al.

(10) Patent No.: US 12,121,754 B2
(45) Date of Patent: Oct. 22, 2024

(54) PARTICLE BEAM IRRADIATION SYSTEM AND PARTICLE BEAM IRRADIATION FACILITY

(71) Applicant: Hitachi High-Tech Corporation, Tokyo (JP)

(72) Inventors: Kenichi Takizawa, Tokyo (JP); Hideaki Nishiuchi, Tokyo (JP); Tadashi Katayose, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 207 days.

(21) Appl. No.: 17/638,950

(22) PCT Filed: Jun. 25, 2020

(86) PCT No.: PCT/JP2020/025029
§ 371 (c)(1),
(2) Date: Feb. 28, 2022

(87) PCT Pub. No.: WO2021/049131
PCT Pub. Date: Mar. 18, 2021

(65) Prior Publication Data
US 2022/0288421 A1    Sep. 15, 2022

(30) Foreign Application Priority Data

Sep. 12, 2019   (JP) ................................. 2019-166000

(51) Int. Cl.
*A61N 5/10*   (2006.01)
(52) U.S. Cl.
CPC ......... *A61N 5/1077* (2013.01); *A61N 5/1049* (2013.01); *A61N 2005/1085* (2013.01)
(58) Field of Classification Search
CPC ................ A61N 5/1077; A61N 5/1049; A61N 2005/1085
See application file for complete search history.

(56) References Cited

U.S. PATENT DOCUMENTS

2011/0220809 A1   9/2011  Yajima et al.
2012/0228522 A1   9/2012  Sasai
(Continued)

FOREIGN PATENT DOCUMENTS

EP   3468665 A1   4/2019
JP   7-272900     10/1995
(Continued)

OTHER PUBLICATIONS

International Search Report of PCT/JP2020/025029 dated Sep. 29, 2020.

(Continued)

*Primary Examiner* — Dixomara Vargas
(74) *Attorney, Agent, or Firm* — MATTINGLY & MALUR, PC

(57) ABSTRACT

An installation area of a particle beam treatment system is reduced. The particle beam irradiation system includes an accelerator which is installed on a floor surface and accelerates a charged particle beam, a transport device which transports the charged particle beam emitted from the accelerator, an irradiation device which irradiates an irradiation target with the charged particle beam transported by the transport device, and a gantry which is installed on the floor surface, and to which the irradiation device is attached. The gantry includes a rotating body which rotates the irradiation device about the irradiation target, and a support device which supports the rotating body from the floor surface at a position where a projection plane of the rotating body on the floor surface and a projection plane of the accelerator or the transport device on the floor surface at least partially overlap with each other.

14 Claims, 6 Drawing Sheets

(56) References Cited

U.S. PATENT DOCUMENTS

| | | | |
|---|---|---|---|
| 2014/0319383 A1 | 10/2014 | Yajima et al. | |
| 2015/0087883 A1 | 3/2015 | Boudreau et al. | |
| 2015/0161793 A1* | 6/2015 | Takahashi | A61N 5/1077 600/1 |
| 2015/0297918 A1* | 10/2015 | Aoki | A61N 5/1081 600/1 |
| 2018/0104510 A1 | 4/2018 | Elgart et al. | |
| 2018/0236268 A1* | 8/2018 | Zwart | A61N 5/107 |
| 2018/0289981 A1* | 10/2018 | Nagamoto | A61B 6/0442 |
| 2018/0326226 A1 | 11/2018 | Ebina et al. | |
| 2019/0299029 A1* | 10/2019 | Inoue | A61N 5/1081 |
| 2021/0393985 A1* | 12/2021 | Hirayama | A61N 5/1049 |
| 2022/0272827 A1* | 8/2022 | Zhang | G21K 1/046 |

FOREIGN PATENT DOCUMENTS

| | | |
|---|---|---|
| JP | 2011-182987 A | 9/2011 |
| JP | 2018-187308 A | 11/2018 |
| WO | 2013/108534 A1 | 7/2013 |
| WO | 2015/042525 A1 | 3/2015 |
| WO | 2015/071430 A1 | 5/2015 |
| WO | 2017/212290 A1 | 12/2017 |

OTHER PUBLICATIONS

Extended European Search Report received in corresponding European Application No. 20862026.0 dated Aug. 23, 2023.

\* cited by examiner

PARTICLE BEAM IRRADIATION SYSTEM AND PARTICLE BEAM IRRADIATION FACILITY

TECHNICAL FIELD

The present invention relates to a particle beam irradiation system and a particle beam irradiation facility.

BACKGROUND ART

Radiation treatment is a treatment method for irradiating an affected part with radiation such as an X-ray or a particle beam. Among devices for radiation treatment, an X-ray treatment device is most widely used. However, since the X-ray passes through a body with a maximum and attenuation dose on a body surface, there is a concern that normal tissues in front of and behind the tumor are influenced. On the other hand, the particle beam has a high dose distribution in a deep range called a Bragg curve. In particle beam treatment, due to the utilization of a feature that a dose is not applied to a portion deeper than the high dose distribution (Bragg peak), the particle beam is irradiated by adjusting the Bragg peak to a position of the affected part and enhancing a dose concentration. The particle beam treatment can suppress an influence on a periphery of the affected part while enhancing the dose concentration to the affected part as compared with X-ray treatment. Further spread of a particle beam treatment system for realizing such a treatment is required.

However, the particle beam treatment system is more expensive than the X-ray treatment device, and a large installation area also hinders the spread of the particle beam treatment system. In order to further spread the particle beam treatment system, it is required to reduce the installation area, the size, and the price of the particle beam treatment system.

PTL 1 discloses a miniaturized particle beam treatment system. The particle beam treatment system includes a synchrotron that accelerates a charged particle beam, a high energy beam transport system that transports the charged particle beam accelerated by the synchrotron, and a rotating gantry including an irradiation field forming device that irradiates a patient with the charged particle beam transported by the high energy beam transport system. In the technology disclosed in PTL 1, the high energy beam transport system that transports the charged particle beam between the synchrotron and the rotating gantry is constructed such that a center of an orbit of the charged particle beam from the synchrotron and a center of rotation of the rotating gantry are on substantially the same straight line, and thus, the installation area of the particle beam treatment system is reduced.

CITATION LIST

Patent Literature

PTL 1: JP 2018-187308 A

SUMMARY OF INVENTION

Technical Problem

An object of the present disclosure is to provide a technology for reducing an installation area of a particle beam treatment system.

Solution to Problem

A particle beam irradiation system according to one aspect of the present disclosure includes an accelerator which is installed on a floor surface and accelerates a charged particle beam, a transport device which transports the charged particle beam emitted from the accelerator, an irradiation device which irradiates an irradiation target with the charged particle beam transported by the transport device, and a gantry which is installed on the floor surface, and to which the irradiation device is attached. The gantry includes a rotating body which rotates the irradiation device about the irradiation target, and a support device which supports the rotating body from the floor surface at a position where a projection plane of the rotating body on the floor surface and a projection plane of the accelerator or the transport device on the floor surface at least partially overlap with each other.

Advantageous Effects of Invention

According to one aspect of the present disclosure, it is possible to provide a particle beam irradiation system with a reduced installation area.

DESCRIPTION OF EMBODIMENTS

Hereinafter, embodiments of the present invention will be described with reference to the drawings.

Here, as an example of a particle beam irradiation system that irradiates an irradiation target with a particle beam, a particle beam treatment system that irradiates a cancer tissue of a cancer patient with a particle beam will be described.

Figure 1:
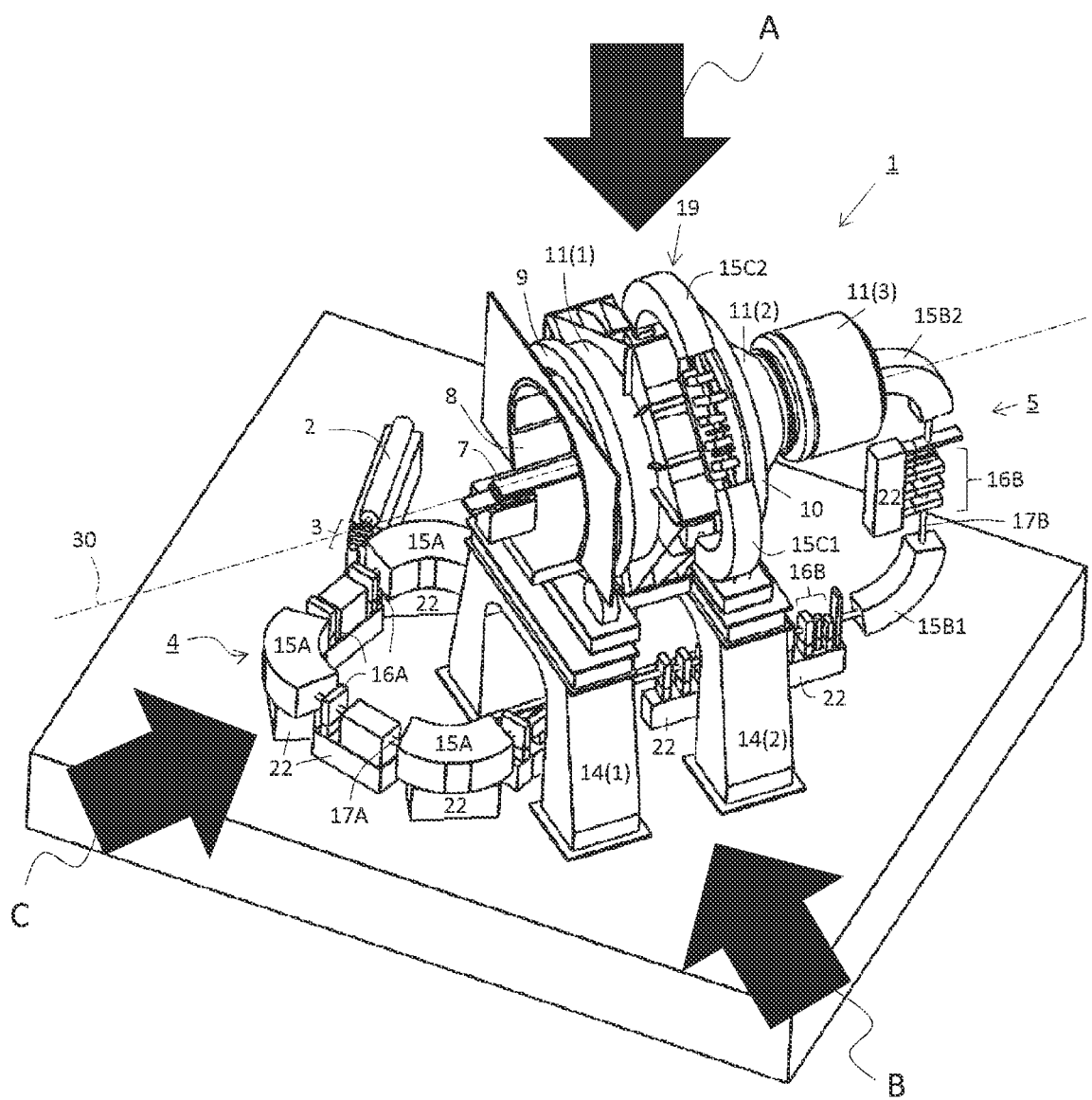
FIG. 1 is a bird's-eye view of a particle beam treatment system.
Figure 2:
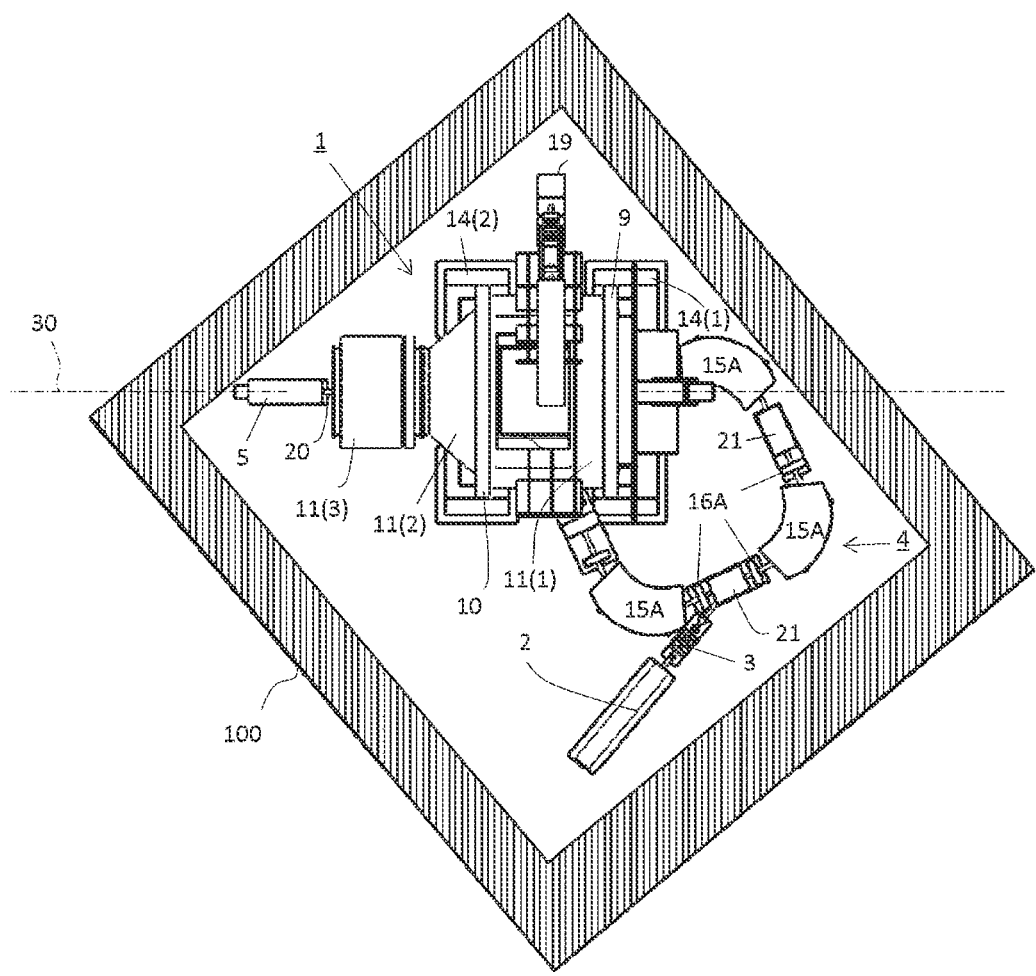
FIG. 2 is a top view of the particle beam treatment system.
Figure 3:
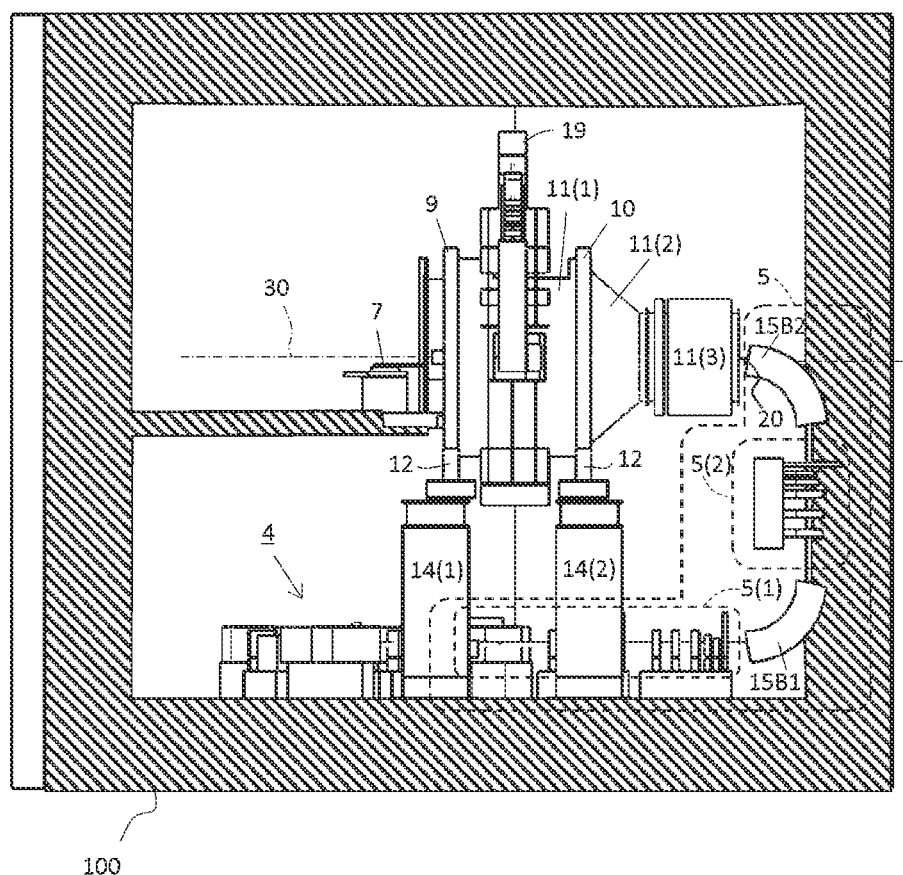
FIG. 3 is a side view of the particle beam treatment system.
Figure 4:
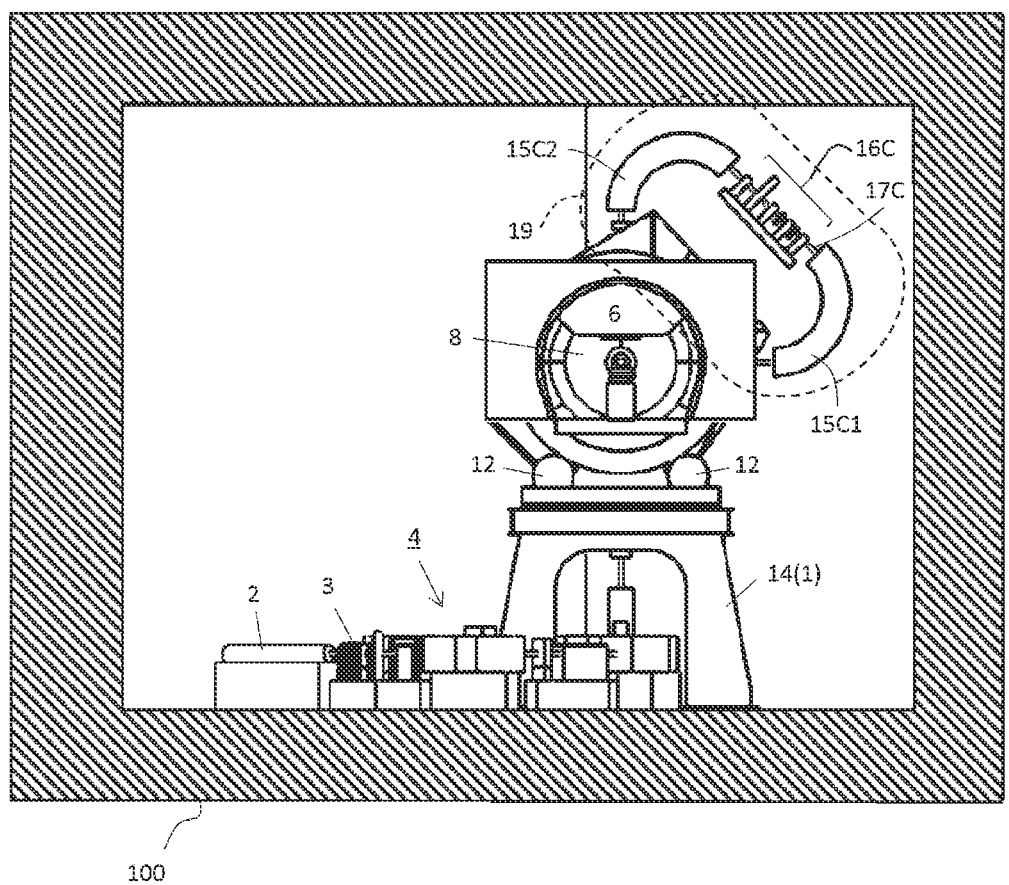
FIG. 4 is a front view of the particle beam treatment system.

FIG. 1 is a bird's-eye view of the particle beam treatment system. FIG. 2 is a top view of the particle beam treatment system, FIG. 3 is a side view of the particle beam treatment system, and FIG. 4 is a front view of the particle beam treatment system. The top view of FIG. 2 is a diagram of the particle beam irradiation system illustrated in FIG. 1 as viewed from a direction of an arrow A. The side view of FIG. 3 is a diagram of the particle beam irradiation system illustrated in FIG. 1 as viewed from a direction of an arrow B. The front view of FIG. 4 is a diagram of the particle beam irradiation system illustrated in FIG. 1 as viewed from a direction of an arrow C.

First, an outline of a configuration and an operation of the particle beam irradiation system will be described.

The particle beam treatment system includes a linear accelerator 2, a low energy beam transport device 3, a synchrotron 4, a high energy beam transport device 5, a rotating gantry 1, and an irradiation nozzle 6.

The linear accelerator 2 accelerates charged particles to generate a charged particle beam. The charged particle beam generated by the linear accelerator 2 is transported by the low energy beam transport device 3 and is incident on the synchrotron 4. The charged particle beam incident on the synchrotron 4 is accelerated to desired energy by the synchrotron 4, and is emitted to the high energy beam transport device 5. The charged particle beam emitted from the synchrotron 4 passes through the high energy beam transport device 5 and is carried to the rotating gantry 1.

The rotating gantry 1 includes a rotating body 11 that rotates about a rotation axis 30, a gantry transport line 19 that is connected to the high energy beam transport device 5 so as to be relatively rotatable with respect to the high energy beam transport device 5 and rotates together with the rotating body 11, and a support device 14 that rotatably supports the rotating body 11.

Referring to the inside of a treatment cage 8 in FIG. 4, the irradiation nozzle 6 that rotates together with the rotating body 11 is installed in the rotating gantry 1. The irradiation nozzle 6 rotates about the rotation axis 30 with a tip facing the rotation axis 30. A treatment stand 7 on which a patient is placed is disposed such that the patient is placed in a direction in which the tip of the irradiation nozzle 6 faces.

The charged particle beam from the high energy beam transport device 5 is transported to the irradiation nozzle 6 by the gantry transport line 19, and an affected part of the patient placed on the treatment stand 7 is irradiated with the charged particle beam from the tip of the irradiation nozzle 6. The irradiation nozzle 6 rotates about the treatment stand 7 by rotating the rotating body 11, and it is possible to change from which direction the charged particle beam is irradiated to the affected part of the patient. In the present embodiment, although a treatment table that includes a top plate on which the patient is placed, three parallel drive mechanisms for driving the top plate in directions of XYZ axes, and a rotation drive mechanism for rotating the top plate about the Z axis is described as an example of the treatment stand 7, the present invention is not limited thereto. For example, another treatment stand such as a robot arm type treatment stand that includes a drive mechanism in a Z-axis direction, a first arm, a first arm turning mechanism, a second arm, a second arm turning mechanism, a top plate, and a rotation mechanism for rotating the top plate in pitch, roll, and yaw may be used.

Next, a configuration and an operation of each device included in the particle beam treatment system will be described.

The linear accelerator 2 includes an ion source and a linear accelerator. The ion source generates charged particles by causing high-speed electrons to collide with a neutral gas. The linear accelerator accelerates charged particles generated by the ion source to a charged particle beam in a state where the charged particles can be accelerated by the synchrotron 4, and emits the charged particle beam toward the low energy beam transport device 3. The charged particle beam is a beam in which charged particles flow thinly. Here, examples of the charged particles include hydrogen, helium, carbon, nitrogen, oxygen, neon, silicon, and argon.

The low energy beam transport device 3 is a device that transports the charged particle beam emitted from the linear accelerator 2 by a space of which the inside is maintained at a high vacuum, and transports the charged particle beam to the synchrotron 4.

The synchrotron 4 is a device that accelerates the charged particle beam from the low energy beam transport device 3 to energy (about 70 MeV to 220 MeV) suitable for cancer treatment through an annular path. The annular path of the synchrotron 4 is formed by connecting bending magnets 15A that deflect the charged particle beam to a predetermined angle, quadrupole magnets 16A that control convergence and/or divergence of the charged particle beam in a horizontal direction and a vertical direction, a vacuum duct 17A that is a path of the charged particle beam, and a radio-frequency acceleration cavity 21 that accelerates the charged particle beam. In the present embodiment, four bending magnets 15A that deflect the charged particle beam by 90 degrees are arranged at four corners, and the vacuum duct 17A penetrates the bending magnets 15A to form an annular path.

In the present embodiment, a method of fixing the bending magnets 15A, the quadrupole magnets 16A, and the radio-frequency acceleration cavity 21 on a frame 22 installed on a floor surface of a building 100 is adopted as a method for fastening the synchrotron 4 in the building 100.

In the present embodiment, although the synchrotron 4 is fastened to the floor surface with the frame 22 interposed therebetween, the synchrotron 4 may be directly installed on the floor surface without using the frame 22.

In the present embodiment, although the configuration in which the four bending magnets 15A are arranged in the annular path is illustrated, the configuration of the synchrotron 4 is not limited thereto. The number of bending magnets 15A in the synchrotron 4 may be less than four, or may be five or more. In the present embodiment, although a deflection angle of the bending magnet 15A is set to 90 degrees, the configuration of the synchrotron 4 is not limited thereto. The deflection angle of the bending magnet 15A may be another angle. The synchrotron 4 may include devices other than the bending magnets 15A, the quadrupole magnets 16A, and the radio-frequency acceleration cavity 21 on the annular path, at a connection portion between the annular path and the low energy beam transport device 3 or at a connection portion between the annular path and the high energy beam transport device 5.

In the present embodiment, although the example in which the charged particle beam is accelerated by using the linear accelerator 2 and the synchrotron 4 as accelerators is illustrated, the present invention is not limited to this configuration. As another example, other accelerators such as a cyclotron, a synchrocyclotron, and a circular accelerator that emits a charged particle beam of any energy by decentering an orbit for accelerating the charged particle beam may be used.

The charged particle beam accelerated by the synchrotron 4 is sent to the high energy beam transport device 5.

The high energy beam transport device 5 is a device that transports the charged particle beam accelerated by the synchrotron 4 to the rotating gantry 1 while deflecting the charged particle beam. The high energy beam transport device 5 is constituted by combining bending magnets 15B, quadrupole magnets 16B, and a vacuum duct 17B.

As illustrated in FIG. 3, the high energy beam transport device 5 includes a first beam transport unit 5(1) that transports the charged particle beam substantially horizontally and a second beam transport unit 5(2) that transports the charged particle beam substantially vertically. The high energy beam transport device 5 includes a bending magnet 15B1 that defects the charged particle beam by 90 degrees between the first beam transport unit 5(1) and the second beam transport unit 5(2), and includes a bending magnet 15B2 that defects the charged particle beam by 90 degrees between the second beam transport unit 5(2) and the rotating gantry 1.

The first beam transport unit 5(1) has a configuration in which the substantially linear vacuum duct 17B penetrates the quadrupole magnets 16B that control the convergence and/or divergence of the charged particle beam. The first beam transport unit 5(1) is fastened to the floor surface with the frame 22 interposed therebetween by fixing the quadrupole magnets 16B on the frame 22 fastened to the floor surface.

Similarly to the first beam transport unit 5(1), the second beam transport unit 5(2) has a configuration in which the substantially linear vacuum duct 17B penetrates the quadrupole magnets 16B. The second beam transport unit 5(2) is fixed and fastened to a wall surface of the building 100 in a state where the quadrupole magnets 16B are fixed to the frame 22. It is possible to reduce an installation area and stabilize the installation by fixing the second beam transport unit 5(2) to the wall surface.

The charged particle beam emitted from the synchrotron 4 is transported to the bending magnet 15B1 by the quadrupole magnets 16B of the first beam transport unit 5(1) and the vacuum duct 17B. For example, a traveling direction of the charged particle beam to be transported is, for example, substantially horizontal to the floor surface, and the first beam transport unit 5(1) connects the synchrotron 4 to the bending magnet 15B1 on a substantially straight line.

The charged particle beam transported from the first beam transport unit 5(1) to the bending magnet 15B1 is deflected in a direction away from the floor surface by the bending magnet 15B1. At this time, for example, a deflection angle of the bending magnet 15B1 is 90 degrees, and a direction in which the deflected charged particle beam is directed is substantially upward in a vertical direction. The charged particle beam deflected by the bending magnet 15B1 is incident on the second beam transport unit 5(2). The second beam transport unit 5(2) transports the incident charged particle beam to the bending magnet 15B2.

The bending magnet 15B2 deflects the charged particle beam from the second beam transport unit 5(2) to the direction of the rotating gantry 1 and causes the charged particle beam to be incident on the rotating gantry 1. At this time, for example, a deflection angle of the bending magnet 15B2 is 90 degrees, and a direction in which the deflected charged particle beam is directed is a direction substantially horizontal to the floor surface and directed to the synchrotron 4. In other words, the charged particle beam from the bending magnet 15B2 is directed in a direction opposite to a direction in which the charged particle beam is emitted from the synchrotron 4.

A connection point between the high energy beam transport device 5 and the rotating gantry 1 is on the rotation axis 30 of the rotating gantry 1, and the traveling direction of the charged particle beam incident on the rotating gantry 1 from the high energy beam transport device 5 coincides with the rotation axis 30 of the rotating gantry.

In the present embodiment, although the configuration in which the high energy beam transport device 5 includes the two bending magnets 15B1 and 15B2 that defect the charged particle beam by 90 degrees has been described as an example, the present invention is not limited to this configuration. As another example, the number of bending magnets 15B may be one or three or more. A deflection angle of the bending magnet 15B is not limited to 90 degrees, and may be another angle. For example, the charged particle beam emitted from the synchrotron 4 may be deflected in a plane substantially horizontal to the floor surface and then may be incident on the bending magnet 15B1. For example, the charged particle beam deflected by the bending magnet 15B2 may be deflected in a plane substantially horizontal to the floor surface and then may be incident on the rotating gantry 1.

In the present embodiment, although the example in which the frame 22 is used for the fastening of the first beam transport unit 5(1) to the floor surface and the fastening of the second beam transport unit 5(2) to the wall surface has been described, the present invention is not limited to this configuration. As another example, the frame 22 may not be used for one or both of the fastening of the first beam transport unit 5(1) to the floor surface and the fastening of the second beam transport unit 5(2) to the wall surface.

In the present embodiment, although the first beam transport unit 5(1) is fastened to the floor surface and the second beam transport unit 5(2) is fastened to the wall surface, the fastening location is not limited thereto. For example, the second beam transport unit 5(2) may be fixed to the support device 14.

The rotating gantry 1 includes a front ring 9, a rear ring 10, the rotating body 11, a support roller 12, a gantry rotation motor (not illustrated), the support device 14, and the gantry transport line 19.

The rotating body 11 includes a first cylindrical portion 11(1), a conical portion 11(2), and a second cylindrical portion 11(3) in order from the front ring 9 side toward the rear ring 10 side. The front ring 9 and the rear ring 10 are connected by the first cylindrical portion 11(1). The front ring 9 side of the rotating body 11 is opened, and the treatment cage 8 which is a space for irradiating the patient with the charged particle beam and treating the patient is provided inside the rotating body 11 and on the front ring 9 side. The gantry transport line 19 is fixed to the rotating body 11.

The support device 14 is fastened to the same floor surface as the synchrotron 4. The support roller 12 is rotatably fixed to the support device 14. The front ring 9 and the rear ring 10 are mounted on the support roller 12. That is, the support device 14 supports the front ring 9, the rear ring 10, the rotating body 11, and the gantry transport line 19 with the support roller 12 interposed therebetween.

The front ring 9, the rear ring 10, the rotating body 11, and the gantry transport line 19 are integrally rotated about the rotation axis 30 by rotating the support roller 12 by power of the gantry rotation motor and transmitting the power to the front ring 9 and the rear ring 10.

Figure 5:
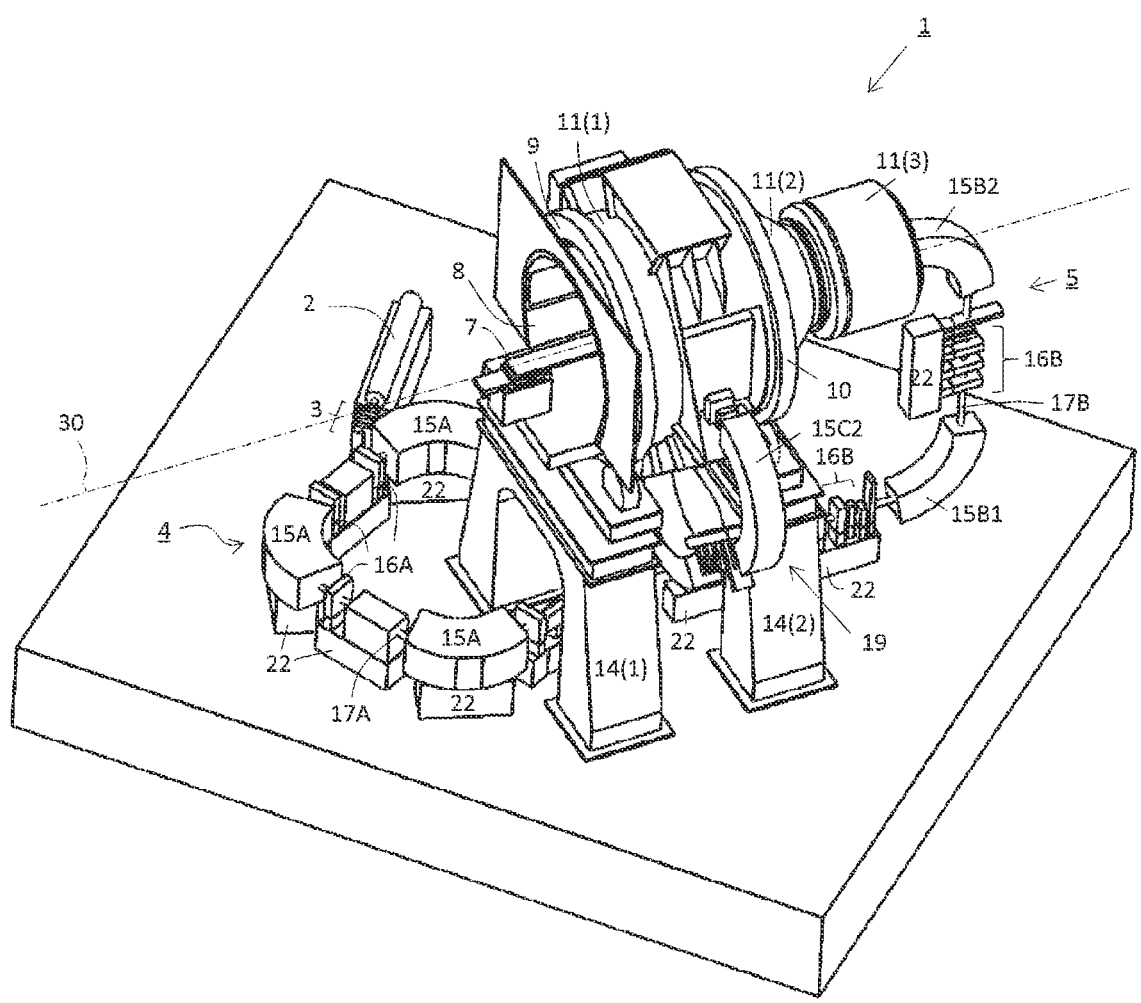
FIG. 5 is a diagram illustrating the particle beam treatment system in a state where a rotating body rotates.

FIG. 5 is a diagram illustrating the particle beam treatment system in a state where the rotating body rotates. FIGS. 1 to 4 illustrate the particle beam treatment system in a state where the irradiation nozzle 6 can irradiate the patient placed on the treatment stand 7 with the charged particle beam from above in the vertical direction. From this state, the rotating body 11 is rotatable by approximately 360 degrees. FIG. 5 illustrates a state where the rotating body 11 rotates 90 degrees clockwise as viewed from the front and the irradiation nozzle 6 can irradiate the charged particle beam in the horizontal direction from the side of the patient.

The gantry transport line 19 is a device that transports the charged particle beam incident from the high energy beam transport device 5 to the irradiation nozzle 6 while deflecting the charged particle beam. The gantry transport line 19 is rotatably connected with the high energy beam transport device 5 at a connection point 20 on the rotation axis 30. The gantry transport line 19 is constituted by combining a plurality of members including bending magnets 15C, a quadrupole magnet 16C, and a vacuum duct 17C.

The gantry transport line 19 causes the charged particle beam incident in the traveling direction along the rotation axis 30 from the high energy beam transport device to pass through the inside of the second cylindrical portion 11(3) and deflects the charged particle beam in a direction away from the rotation axis 30 by a bending magnet (not illustrated). The gantry transport line 19 transports the charged particle beam deflected in the direction away from the rotation axis 30 to the outside of the rotating body 11.

On the outside of the rotating body 11, a portion constituted by a bending magnet 15C1, the quadrupole magnet 16C, the vacuum duct 17C, and a bending magnet 15C2 is attached to an outer peripheral surface of the first cylindrical portion 11(1). The charged particle beam that exits to the outside of the rotating body 11 is deflected by the bending magnet 15C1 at a deflection angle of 135 degrees in a plane perpendicular to the rotation axis 30, and is transported in a circumferential direction of the rotating body 11 by the vacuum duct 17C while the spread of the beam is controlled by the quadrupole magnet 16C. The charged particle beam transported by the vacuum duct 17C is deflected by the bending magnet 15C2 by 135 degrees in a direction directed to the rotation axis 30 in a plane perpendicular to the rotation axis 30. The charged particle beam deflected in the direction directed to the rotation axis 30 enters the inside of the rotating body 11 and is irradiated to the patient in the treatment cage 8 with the irradiation nozzle 6 interposed therebetween.

By the gantry transport line 19 having the aforementioned configuration, a length of the rotation axis 30 of the rotating gantry 1 in a front-rear direction can be shortened, and the installation area of the particle beam treatment system can be reduced. Here, the installation area of the particle beam treatment system is a floor surface area required for installing the particle beam treatment system.

In the present embodiment, although the configuration in which the gantry transport line 19 includes the three bending magnets is illustrated, the configuration of the gantry transport line 19 is not limited thereto. The number of bending magnets in the gantry transport line 19 may be less than three, or may be four or more. In the present embodiment, deflection angles of the bending magnets 15C1 and 15C2 are set to 135 degrees, but the present invention is not limited thereto. The bending angles of the bending magnets 15C1 and 15C2 may be other angles. The gantry transport line 19 may include devices other than the bending magnets 15C, the quadrupole magnet 16C, and the vacuum duct 17C.

In the present embodiment, although the gantry transport line configured to transport the charged particle beam in the circumferential direction of the rotating body 11 while controlling the convergence and/or divergence of the charged particle beam has been illustrated, the present invention is not limited to this configuration. As another example, the gantry transport line 19 may be configured to deflect the charged particle beam incident in the traveling direction along the rotation axis 30 from the high energy beam transport device 5 in the direction away from the rotation axis 30, deflect the charged particle beam deflected in the direction away from the rotation axis 30 in a direction substantially parallel to the rotation axis 30, and deflect the charged particle beam deflected in the direction substantially parallel to the rotation axis 30 in the direction directed to the rotation axis 30.

When the rotating gantry 1 rotates and the gantry transport line 19 is positioned below, the support device 14 has such a height that the gantry transport line 19 is not in contact with the synchrotron 4 or the first beam transport unit 5(1) of the high energy beam transport device 5. More specifically, a height of the support device 14 from the flow surface is higher than a total value of a height of the synchrotron 4 below the bending magnet 15C1 and the bending magnet 15C2 of the gantry transport line 19 or the high energy beam transport device 5 from the floor surface of the device and a maximum value of a height from the bending magnet 15C1 or the bending magnet 15C2 from the outer peripheral surface of the first cylindrical portion 11(1).

The rotating gantry 1 and the synchrotron 4 can be arranged on the same floor surface with the installation area overlapping each other by providing a sufficient height to the support device 14, and the installation floor area of the entire particle beam treatment system can be reduced. A sufficient height is provided to the support device 14, and thus, it is not necessary to lower the floor surface of the building 100 while the floor surface is conventionally lowered only in a passage region of the gantry transport line in order to avoid the contact between the gantry transport line and the floor surface. As a result, the building 100 can have a simple configuration.

In the present embodiment, the support device 14 has four legs, and the four legs support the rotating body 11. In the present embodiment, the support device 14 includes a first support device 14(1) and a second support device 14(2). Both the first support device 14(1) and the second support device 14(2) have an arch shape having two legs, and are arranged in a direction of the rotation axis 30. The first support device 14(1) is on the front ring 9 side, and the second support device 14(2) is on the rear ring side. The first support device 14(1) is disposed in front of the bending magnet 15C1 and the bending magnet 15C2 of the gantry transport line 19. The second support device 14(2) is disposed behind the bending magnet 15C1 and the bending magnet 15C2 of the gantry transport line 19. When the rotating body 11 rotates, the gantry transport line 19 that rotates together with the rotating body 11 can pass between the first support device 14(1) and the second support device 14(2) by constituting the support device 14 by the front first support device 14(1) and the rear second support device 14(2) in this manner, and collision between the support device 14 and the transport line 19 can be avoided. The first support device 14(1) supports the support roller 12 on which the front ring 9 is mounted. The second support device 14(2) supports the support roller 12 on which the rear ring 10 is mounted.

In the first support device 14(1), one leg is disposed on a floor surface inside a circular ring of the synchrotron 4, the other leg is disposed on a floor surface outside the circular ring, and the circular ring of the synchrotron 4 passes between the legs of the first support device 14(1) and passes through an arch space. In other words, the first support device 14(1) is disposed across the circular ring of the synchrotron 4. The high energy beam transport device 5 is disposed to pass between the legs of the second support device 14(2) and pass through the arch space. In other words, the second support device 14(2) is disposed to across the high energy beam transport device 5. As a result, the synchrotron 4 and a part of the high energy beam transport device 5 can be arranged below the rotating body 11. The synchrotron 4 and/or the high energy beam transport device 5 can be arranged in a portion where the support device 14 is not in contact with the floor surface between a grounding surface where the support device 14 is in contact with the floor surface and another grounding surface where the support device 14 is in contact with the floor surface, and the installation area of the entire particle beam treatment system can be reduced.

In particular, in the configuration in which the charged particle beam emitted from the synchrotron 4 below the first support device 14(1) in front passes between the two legs of the second support device 14(2), is transported backward, and is transported backward and upward by the high energy beam transport device 5, the synchrotron 4 and the high energy beam transport device 5 are efficiently arranged below the rotating body 11, and the installation area of the particle beam treatment system is reduced.

The configuration and the disposition of the support device 14 are not limited to the present embodiment. The rotating body 11 may be disposed at a position higher than at least a part of the linear accelerator 2, the synchrotron 4, or the high energy beam transport device 5. When at least a part of the linear accelerator 2, the synchrotron 4, or the high energy beam transport device 5 is disposed below the rotating body 11, the installation area of the entire particle beam treatment system can be further reduced. The installation area can be reduced by disposing the high energy beam transport device 5 extending substantially in the vertical direction. However, the linear accelerator 2, the synchrotron 4, or the high energy beam transport device 5 may not be disposed below the rotating body 11. A space for installing a control device and a power supply can be secured below the rotating body by disposing the rotating body 11 at a high position, and the installation area of the entire particle beam treatment system can be reduced.

In the present embodiment, although the four legs of the support device have been described as an example, the number of legs is not limited to four, and may be three or less, or five or more. In the present embodiment, although the arch-shaped first support device and the arch-shaped second support device have been described as an example, the first support device 14(1) and the second support device 14(2) may have an integrated structure, or some or all of the legs may have separate structures.

A material of the support device 14 may be metal such as iron, or another material such as concrete may be used partially or entirely. When the material of the support device 14 is metal, the support device 14 can be fastened after the synchrotron 4 and the high energy beam transport device 5 are fastened, and the synchrotron 4 and the high energy beam transport device 5 can be easily fastened. On the other hand, the material of the support device 14 is concrete, and the support device is disposed between a control device (not illustrated) of the particle beam treatment system and the synchrotron 4 or the high energy beam transport device 5. Thus, the support device can also function as a shielding wall of the control device.

In the present embodiment, although the example in which the rotating gantry 1 rotates by approximately 360 degrees has been described, a rotation angle may be 360 degrees or less, and another gantry such as a half gantry having a rotation angle of 300 degrees or less may be used.

The rotating gantry 1 includes the support device 14 described above, and thus, it is possible to arrange the devices such that a region where the linear accelerator 2, the synchrotron 4, and the high energy beam transport device 5 are installed and a region where the rotating gantry 1 is installed are vertically overlapped. As a result, it is possible to reduce the installation area of the entire particle beam treatment system. In other words, the device can be disposed such that at least a part of a projection plane of the linear accelerator 2, the synchrotron 4, and the high energy beam transport device 5 on the floor surface overlaps with at least a part of a projection plane of the rotating gantry 1 on the floor surface, and the installation area of the entire particle beam treatment system can be reduced.

The irradiation nozzle 6 is a device that processes the charged particle beam transported from the high energy beam transport device 5 into a suitable dose distribution according to a shape of a cancer tissue of the patient and irradiates the affected part with the charged particle beam. The irradiation nozzle 6 is attached to the rotating body 11 of the rotating gantry 1, and rotates about the rotation axis 30 integrally with the rotating body 11. Thus, the patient in the treatment cage 8 can be irradiated with the charged particle beam from any direction.

Figure 6:
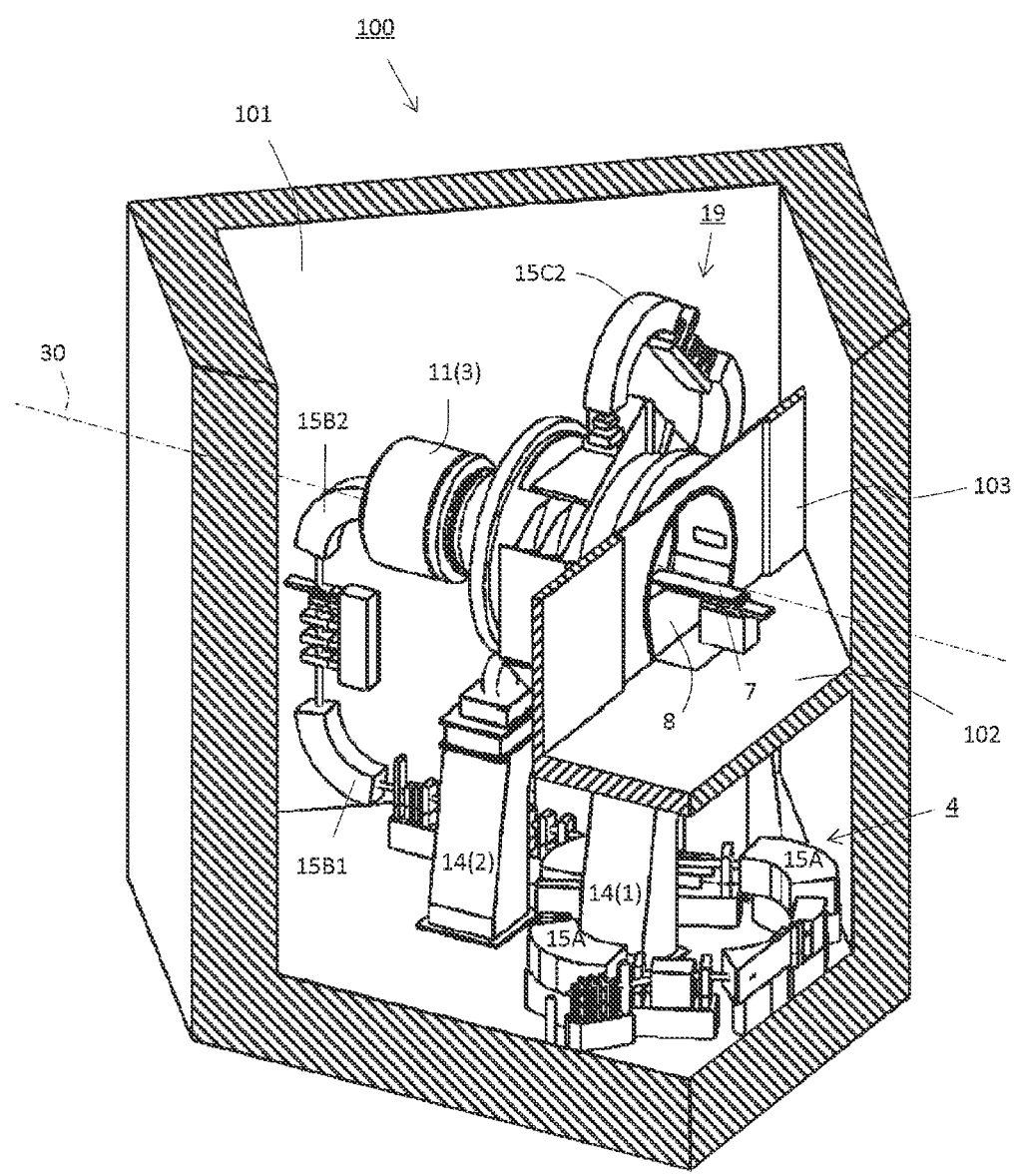
FIG. 6 is a diagram illustrating a state where the particle beam treatment system is installed in a building.

FIG. 6 is a diagram illustrating a state where the particle beam treatment system is installed in the building.

The particle beam treatment system is installed in the building 100 that is a structure, and the particle beam treatment system and the building 100 constitute a particle treatment facility. An accelerator room 101 and a treatment room 102 separated from each other by a treatment room wall 103 are provided in the building 100. The linear accelerator 2, the synchrotron 4, the high energy beam transport device 5, and the rotating gantry 1 are fastened to the accelerator room 101. The treatment stand 7 on which the patient is placed is installed in the treatment room 102. The treatment stand 7 can be taken in and out of the treatment cage 8 from an opening of the treatment room wall 103.

In the accelerator room 101, a space having a rotation radius from the rotation axis 30 is secured such that the rotating gantry 1 can freely rotate by approximately 360 degrees. A space on a diagonal line of the building 100 can be used by disposing the rotating gantry 1 such that the rotation axis 30 forms an oblique angle with respect to an outer wall of the building 100, and the installation area can be further reduced. For example, as illustrated in FIG. 2, the rotation axis 30 is disposed along the diagonal line of the building 100 with respect to the substantially rectangular building 100.

In the present embodiment, although the example in which the linear accelerator 2, the synchrotron 4, the high energy beam transport device 5, and the rotating gantry 1 are installed in the accelerator room 101 has been described, the present invention is not limited thereto. For example, the linear accelerator 2 or the high energy beam transport device 5 may be installed in another room other than the accelerator room 101. A control device (not illustrated) may be disposed in the accelerator room 101. At this time, a shielding wall between the synchrotron 4 and the control device may be provided in the accelerator room 101.

In the present embodiment, the synchrotron 4 is described as an example of an accelerator. The synchrotron 4 can accelerate the charged particle beam to any energy and can emit the charged particle beam of any energy. On the other hand, the cyclotron or the synchronous cyclotron that is another accelerator can emit only a charged particle beam accelerated to maximum energy. In the cyclotron or the synchronous cyclotron, the charged particle beam emitted with the maximum energy is caused to pass through a device called a degrader, so that the energy is reduced to any value and the patient is irradiated with the charged particle beam. At this time, a dilator radiates to absorb energy. Thus, in the case of the cyclotron, it is necessary to provide a thick radiation wall between the gantry on which the patient is placed and the accelerator in order to reduce an exposure dose of the patient. On the other hand, the synchrotron 4 that does not require the dilator does not require the radiation wall like the cyclotron or the synchrocyclotron, and the accelerator and the rotating gantry 1 can be installed in the same room.

The accelerator and the rotating gantry 1 can be installed in the same room in this manner, and thus, the height of the building 100 can be suppressed. As a result, the downsizing and cost reduction of the particle beam treatment facility can be realized. However, not only the synchrotron 4 but also any accelerator capable of emitting any energy can provide an effect of reducing the installation area.

Neutrons and the like generated from an accelerator having a circular or circular ring shape have directivity in an outer circumferential direction of the circle. Since the treatment cage 8 and the synchrotron 4 are not positioned on the same plane, there are few neutrons generated from the synchrotron 4 toward the patient on the treatment stand 7, and the floor surface of the treatment room 102 and the treatment room wall 103 may not be thickened like the radiation wall.

Since a floor level of the treatment room 102 is set in the vicinity of the rotation axis 30 in which a space of the rotation radius is secured, the floor level is usually about 6 m to 8 m higher than a floor level of the accelerator room 101.

In the present embodiment, although the configuration in which one rotating gantry 1 and one treatment room 102 are provided has been described as an example, the present invention is not limited thereto. Two or more rotating gantries 1 may be installed in the accelerator room 101, and two or more treatment rooms 102 may be provided in the building 100.

The above-described embodiment is an example for description, and is not intended to limit the scope of the present invention to the embodiment. Those skilled in the art can implement the present invention in various other aspects without departing from the scope of the present invention.

REFERENCE SIGNS LIST 1 rotating gantry
2 linear accelerator
3 low energy beam transport device
4 synchrotron
5 beam transport device
6 irradiation nozzle
7 treatment stand
8 treatment cage
9 front ring
10 rear ring
11 rotating body
12 support roller
14 support device
15 bending magnet
16 quadrupole magnet
17 vacuum duct
19 gantry transport line
20 connection point
21 radio-frequency acceleration cavity
22 frame
30 rotation axis
100 building
101 accelerator room
102 treatment room
103 treatment room wall

The invention claimed is:

1. A particle beam irradiation system, comprising:
an accelerator which is installed on a floor surface and accelerates a charged particle beam;
a transport device which transports the charged particle beam emitted from the accelerator;
an irradiation device which irradiates an irradiation target with the charged particle beam transported by the transport device; and
a gantry which is installed on the floor surface, separately from the accelerator, and to which the irradiation device is attached,
wherein the gantry includes:
a rotating body which rotates the irradiation device about the irradiation target, and
a support device which supports the rotating body from the floor surface at a position where a projection plane of the rotating body on the floor surface and a projection plane of the accelerator or the transport device on the floor surface at least partially overlap with each other,
wherein the transport device includes a first beam transport unit which transports the charged particle beam accelerated by the accelerator along the floor surface and a second beam transport unit which transports the charged particle beam upward on a downstream side of the first beam transport unit, and
wherein the support device has the second beam transport unit behind and is grounded on the floor surface across the first beam transport unit by two legs.

2. The particle beam irradiation system according to claim 1,
wherein the accelerator and the gantry are arranged in one space partitioned as a room.

3. The particle beam irradiation system according to claim 2,
wherein the support device is in contact with the floor surface on a first grounding surface and a second grounding surface, at least a part of at least one of the accelerator or the transport device is disposed between the first grounding surface and the second grounding surface.

4. The particle beam irradiation system according to claim 1,
wherein the transport device includes a first bending magnet which deflects the charged particle beam accelerated by the accelerator upward and a second bending magnet which deflects the charged particle beam deflected by the first bending magnet in a direction of a rotation axis of the rotating body.

5. The particle beam irradiation system according to claim 1,
wherein the gantry further includes a third bending magnet which deflects the charged particle beam on an outside of an outer peripheral surface of the rotating body, and
wherein the support device includes a first support unit which is disposed in front of the third bending magnet in a rotation axis direction of the rotating body and a second support unit which is disposed behind the third bending magnet.

6. The particle beam irradiation system according to claim 1,
wherein the gantry further includes a transport line which transports the charged particle beam to an outer peripheral surface of the rotating body, and
wherein a height of the support device is larger than a sum of a height of the transport line from the outer peripheral surface of the rotating body and a height of the accelerator or the transport device below the rotating body from the floor surface.

7. The particle beam irradiation system according to claim 1,
wherein a part of the transport device is fixed to a wall surface of a room in which the particle beam irradiation system is installed.

8. The particle beam irradiation system according to claim 1,
wherein the gantry further includes a transport line which transports the charged particle beam transported by the transport device to an outside of an outer peripheral surface of the rotating body, transports the charged particle beam in a circumferential direction of the rotating body, and transports the charged particle beam in a direction directed to a rotation axis of the rotating body.

9. The particle beam irradiation system according to claim 1,
wherein the accelerator is a synchrotron that accelerates the charged particle beam on an annual path.

10. The particle beam irradiation system according to claim 9,
wherein the support device incudes a first leg and a second leg as the two legs, and is grounded on the floor surface across the annual path such that the first leg is positioned on an inside of the annual path and the second leg is positioned on an outside of the annual path.

11. The particle beam irradiation system according to claim 1,
wherein at least a part of a material of the support device is metal.

12. The particle beam irradiation system according to claim 1,
wherein at least a part of a material of the support device is concrete.

13. A particle beam irradiation facility, comprising:
a building; and
the particle beam irradiation system according to claim 1 installed in the building.

14. The particle beam irradiation facility according to claim 13,
wherein the irradiation target is a patient, and
wherein the particle beam irradiation facility further includes a treatment room in which a treatment stand on which the patient is placed and which is able to enter an inside of the rotating body is installed and a partition wall provided between the accelerator and a room where the gantry is installed.

* * * * *